United States Patent [19]

Lippmann et al.

[11] 4,259,315
[45] Mar. 31, 1981

[54] CONTROLLED RELEASE POTASSIUM DOSAGE FORM

[75] Inventors: Irwin Lippmann; Shankar D. Popli; Larry G. Miller; Louis G. Bell, all of Richmond, Va.

[73] Assignee: A. H. Robins Company, Inc., Richmond, Va.

[21] Appl. No.: 159,335

[22] Filed: Jun. 13, 1980

[51] Int. Cl.$^3$ .......................... A61K 9/48; A61K 9/50; A61K 33/14

[52] U.S. Cl. ........................................ 424/37; 424/32; 424/33; 424/35; 424/153; 424/19

[58] Field of Search ....................... 424/19, 32, 33, 35, 424/37, 153

[56] References Cited

FOREIGN PATENT DOCUMENTS 817670 1/1975 Belgium .

OTHER PUBLICATIONS

Sandell, E., Acta Pharm. Suecica 4(3): 223-235 (1967) Tolerance to Ammonium Potassium and Sodium Chloride in Hard Gelatin Capsules Chem. Abstr. 67:52628p (1967).

Maggi G. C. et al., Curr. Ther. Res. Clin. Exp. (1977) 21(5): 676-680, Therapeutic Activity and Effects on Fecal Blood Loss of a New Micro-Encapsulated Potassium Chloride Prepn. GA 87:96182f (1977).

Renker H., Arzneim. Forsch. (1977) 27(4): 845-851, Tolerance Study of Different Oral Potassium Prepns. In Rats C.A. 87:58471s (1977), (Microencapsulated KCl Sustained Release Tablets).

Maggi G. C. et al., Expo-Congr. Int. Technol. Pharm, 1st (1977) 3:132-143 (FR) Presentation of Some Advantages of Microencapsulation Applied to Drugs C.A. 90:43762A (1979).

Primary Examiner—Shep K. Rose

[57] ABSTRACT

Pharmaceutical compositions for treating potassium deficiency in monogastric animals comprising gelatin capsules containing mixture comprised of controlled release form of microencapsulated potassium salt and hydrophilic surfactant are disclosed.

10 Claims, No Drawings

CONTROLLED RELEASE POTASSIUM DOSAGE FORM

BACKGROUND OF THE INVENTION

1. Field of Invention

The present invention relates to novel pharmaceutical compositions suitable for oral administration to monogastric animals consisting of gelatin capsules containing therein mixtures comprising microencapsulated potassium salt (microcapsules) and hydrophilic surfactant external to the microcapsules and methods of using same. The compositions provide safe and effective, controlled release potassium dosage forms for treating potassium deficiency or prevention of potassium depletion in humans. The inclusion of the surfactant greatly reduces the likelihood for development of local toxicity and severe damage to mucosa in a host having a partial obstruction in the alimentary canal. The microcapsules are non-enteric coated and in mixture with the surfactant are free-flowing when wetted in a restricted space.

2. Description of the Prior Art

Potassium chloride is the salt most frequently employed in order to offset potassium depletion in humans or when the action of the potassium cation is desired. It is used when hypokalemia or hypochloremic alkalosis exists, such as after prolonged diarrhea or vomiting or consequent to adrenal steroid therapy or treatment with certain diuretics, such as the thiazides. It is used to elevate normal plasma potassium levels, such as in the treatment of digitalis intoxication. It may be used as a diuretic.

Potassium chloride is a known irritant to the gastrointestinal tract and administration of the salt may cause nausea, vomiting, epigastric distress, abdominal discomfort and diarrhea. Excessive dosages may cause weakness, listlessness, mental confusion, hypotension, vertigo, heart block and even death. Potassium chloride frequently shows signs of toxicity when administered to humans and must be administered cautiously.

For therapeutic purposes, dosages of potassium chloride of 1 to 2 grams taken 2 to 6 times per day are frequently administered. Various dosage forms of potassium chloride, such as liquids, uncoated and enteric-coated tablets, microcapsules, and the like, have been used in the administration to humans but frequently have been found to cause gastrointestinal ulcers, obstruction, hemorrhage and perforation as well as the symptoms of toxicity previously mentioned due to large concentration of the potassium cation in the system.

Sugar-coated tablets containing potassium chloride in a wax matrix (non-enteric-coated) are marketed as a slowly available potassium source. Physicians Desk Reference (1979), page 794, states "fewer bowel lesions are observed with wax-matrix tablets compared to enteric-coated potassium chloride products, but that there have been reports of upper gastrointestinal bleeding associated with the wax-matrix tablets. Use of these wax-coated products should be discontinued immediately and the possibility of bowel obstruction or perforation considered if severe vomiting, abdominal pain, distention or gastrointestinal bleeding occurs."

The administration of gelatin capsules containing microcapsules having ethyl cellulose as a wall material and potassium chloride as a core material was thought to provide an effective method of supplying potassium cations to humans with a minimum of side effects as compared with other dosage forms. However, it was found that the microencapsulated potassium chloride becomes immobilized during breakdown of the gelatin capsule container and will agglomerate in the alimentary canal. This agglomerate can potentially remain in one location of the alimentary tract, particularly in a partially obstructed narrow passage, and cause damage to the mucosa, such as ulceration and even perforation. In rare cases, stenotic and/or ulcerative lesions may develop due to high concentrations of potassium leaching from immobilized microcapsule agglomerates such as in a partially obstructed duodenum.

Others have used surfactants to improve dissolution rate of drugs when powders agglomerate and teach the rate of dissolution is proportional to the reduction in surface tension of the gastric juice (Remington's Pharmaceutical Sciences, 15th Ed. (1973) p. 297). Others have used surfactants such as Polysorbate 20 as an ingredient interior to microcapsules during preparation of microcapsules and have discussed the adverse effect of such agents on the increased release rate of solids from the microcapsules (Luzzi et al. J. Pharm. Sci. 56 (9), 1174–7 (1967)

Prior to our invention it was not known to combine microencapsulates of potassium salt and hydrophilic surfactant exterior to the microencapsulates in a gelatin capsule to provide a source of controlled release potassium to monogastric animals, relatively free of discomforting side effects in the stomach and free of serious side effects in that small segment of the population who may or may not know they have partial obstruction in the alimentary canal such as in the esophagus or duodenum. Furthermore, it was not known that such combinations would not result in more serious local or general toxic condition in either the stomach or intestines rather than improvement, as it was not known what effect surfactant would have on the interchange of the somewhat toxic potassium ion with the gastric tissue during the absorption process.

The present invention is therefore based on the discovery that mixing hydrophilic surfactant with postassium chloride microcapsules and administered in a capsule will eliminate severe toxicity otherwise caused by the microencapsulated potassium chloride in narrow, partially obstructed passages in the alimentary canal such as the duodenum, while at the same time leaving the rate of potassium chloride release substantially unchanged within a suitable range and creating no new toxicity problems anywhere in the alimentary canal due to mucous barrier upset and exposure to potassium chloride in the presence of surfactant.

SUMMARY OF THE INVENTION AND OBJECTS

The primary object of the present invention provides novel compositions which have important pharmaceutical application in the treatment of potassium deficiency in monogastric animals, particularly humans. The compositions in dosage form consist of a gelatin capsule suitable for oral ingestion containing a mixture comprising a pharmaceutically acceptable microencapsulated potassium salt and a pharmaceutically acceptable hydrophilic surfactant external to the microcapsules in an amount effective to increase the flowability of the microcapsules on contact with liquids in the alimentary canal and to permit flow of the wetted microcapsules through narrow openings such as in a partially obstructed esophagus or duodenum. The surfactant also speeds the disintegration and separation of the gelatin capsule from the microcapsules. Stated another way, addition of surfactant prevents immobilization of microencapsulated potassium salt in a restricted space in the alimentary canal.

The primary function of the compositions of this invention is to provide, upon oral administration to a host, the element potassium in ionized form in a constant controlled supply over about an eight-hour period without concern as to whether or not it is known partial obstruction of alimentary passageways exist. Obviously, the compositions are suitable for administration of potassium salts to a host having normal alimentary canal with benefit in reduced side effects as compared to microcapsules having no surfactant present and mixture of two or more microencapsulated potassium salts may be employed if desired.

Another object is to provide an effective and safe oral dosage form of potassium for humans which will readily be transported through partially obstructed or narrowed channels of the alimentary canal.

Another object is to provide a method of relieving treating or preventing potassium deficiency in humans with minimal adverse side effects comprising orally administering a gelatin capsule containing a mixture comprised of controlled-release form of microencapsulated sale and hydrophilic surfactant external to the microencapsulated salt.

Additional objects will become apparent hereinafter and still other objects will be apparent to one skilled in the art.

DETAILED DESCRIPTION OF THE INVENTION

The pharmaceutical compositions of this invention are in the form of capsules. Capsules are solid dosage forms in which the substances, in this instance potassium salt and hydrophilic surfactant, are enclosed in either a hard or soft soluble container or shell of a suitable form of gelatin. The capsules may be used in a variety of sizes and shapes, it only being necessary that the capsule be large enough to accommodate the particular dosage amount used. Capsule filling may be done by hand or machine and such procedures are well known in the art. To insure uniformity in weight of microcapsules in the filling of the capsules, particularly by machine, a lubricant such as magnesium or aluminum stearate may be added to the formulation, usually in a tumbling apparatus, to aid in the processing thereof. Remington's Pharmaceutical Sciences, 15th Ed. (1973), at pages 1598–1605, contains a detailed explanation of capsule preparation.

The microcapsules useful for the purposes of this invention are those which have a pharmaceutically acceptable polymeric material as an outer or coating material with a potassium salt as an inner or core material. The microcapsules will normally contain from about 3 to 50 percent by weight of the polymeric material and about 50 to 97 percent by weight of a potassium salt. Preferably, the microcapsules will contain from about 10 to 25 percent by weight of the polymeric material and about 75 to 90 percent by weight of a potassium salt. The microcapsules useful for the purpose of this invention may be prepared by any known microencapsulation process. These are processes or techniques wherein thin coatings may be applied reproducibly to small particles of solids, droplets of liquids, or dispersions forming microcapsules. These methods may be distinguished readily from other coating procedures in that the size of the particles obtained can be very small, for example, a micron in size, and will have the properties of a free-flowing powder. It is only necessary for the purposes of this invention that the thin coatings be comprised of the polymeric material and the particles being coated be comprised of the potassium salt.

One microencapsulation process preferred in the manufacture of the microcapsules useful in the pharmaceutical compositions of this invention is that developed by the NCR Corp., USA. This process is chemical in nature based on phase separation or coacervation techniques. This process consists of three steps: (1) formation of three immiscible phases as follows: a liquid manufacturing phase, a core material phase, and a coating material phase; (2) deposition of the coating material on the core material; and (3) solidifying the coating normally by thermal, cross-linking or desolvation techniques, to form a microcapsule. Film thickness of the coating material may be varied considerably depending upon the surface area of the core material and other physical characteristics of the system. Upon isolation and drying, the microcapsule particles appear as free-flowing powder suitable for formulation in capsules. U.S. Pat. No. 3,415,758 to Powell et al., issued Dec. 10, 1968, discloses a suitable method of preparing the polymer coated potassium salt microcapsules suitable for purposes of this invention.

The polymeric materials suitable for use as outer or wall materials in the microcapsules useful in the compositions of this invention should be hydrophobic and capable, in solution, of wetting the potassium salt core material in order to deposit and form a wall around the core entities during the formation of the microcapsules. Suitable polymeric wall-forming materials are ethyl cellulose, cellulose nitrate, cellulose acetate phthalate, polymethyl methacrylate acrylonitrilestyrene copolymers, polystyrenes, vinylidene chloride-acrylonitrile copolymers, epoxy resins and the like. It is preferred that the polymeric wall-forming material be ethyl cellulose, particularly an ethyl cellulose having an ethoxyl content of about 47.5 by weight and a viscosity of 22 centipoises in a 5% concentration, by weight, in an 80/20 toluene-ethanol bath at 25° C.

The potassium salts suitable for use as core materials in the microcapsules useful in the compositions of this invention include any potassium salt which adequately provides potassium cations to the human being treated and which may be taken internally. Suitable potassium salts are potassium chloride, potassium iodide, potassium gluconate, potassium acetate, potassium citrate, potassium sodium tartrate, potassium phosphate, and the like. The preferred potassium salt for the purposes of this invention is potassium chloride.

Generally, the microcapsules suitable for this invention when combined with a hydrophilic surfactant in an amount selected from the range of 0.05 to 5 weight percent will characteristically release 80 to 100% of the contained potassium salt uniformly over a 6-10 hour time period when tested by the method of USP XIX, p. 651, and described briefly hereinbelow. The microcapsules having this characterization are regarded as controlled-release microencapsulated potassium salt.

The surfactants suitable for use in this invention include surface-active agents having a hydrophobic portion (alkyl chain) and a hydrophilic portion (carboxyl and carboxylate groups). It is only necessary that the surfactant used be of a hydrophilic nature and pharmaceutically acceptable. Any such surfactant or combination thereof having a hydrophile-lipophile balance number (HLB) in excess of 10 is suitable for use in this invention. The HLB value is simply the percentage weight of the hydrophilic group divided by five. For example, a 100% hydrophilic molecule (polyethylene glycol) would have a HLB value of 20. Those surfactants exhibiting HLB values in excess of 20, such as lauryl sulfate, show hydrophilic behavior in excess of the polyoxyethylene groups alone. Examples of surfactants suitable for the purposes of this invention are polyoxyethylene monostearate, Polyethylene Glycol 400 monostearate, triethanolamine oleate, polyoxyethylene alkyl phenol, tragacanth, polyoxyethylene sorbitan monolaurate, polyoxyethylene castor oil, polyoxyethylene sorbitan monooleate, polyoxyethylene sorbitan monopalmitate, polyoxyethylene lauryl ether, polyoxyethylene monostearate, sodium oleate, sodium lauryl sulfate, and the like. Mixtures of surfactants are also suitable for the purposes of this invention, it only being necessary that the blended combined HLB value of the two surfactants be in excess of 10. In this manner a surfactant having a low HLB value may be mixed with a surfactant having a high HLB with the resultant surfactant mixture being suitable for the purposes of this invention.

It is preferred that the surfactant used for the purposes of this invention be selected from those surfactants classified as anionic or nonionic. These surfactants are particularly useful in pharmaceutical systems for their compatibility, stability, and non-toxicity. The surfactant should be present in the pharmaceutical composition of this invention in about 0.05 to 5.0 percent by weight of the microencapsulated potassium salt employed in the composition and preferably in amounts of about 0.05 to 1.0 percent by weight. It is only necessary that the amount of surfactant used be an effective amount; that is, an amount which will adequately increase the flowability of the wetted microcapsules upon administration to humans, particularly those having narrowed passageway in the alimentary canal, to prevent severe localized toxicity effects from developing. Surfactant is usually added to the microcapsules in a tumbling apparatus. Preferred surfactants are sodium lauryl sulfate, Polysorbate 20 and Polysorbate 80.

Description of Microcapsules Tested

The microcapsules used in the examples were prepared from cubic crystals of potassium chloride of mean particle size of 438μ. The crystals were microencapsulated with ethyl cellulose by coacervation with ethyl cellulose to produce microcapsules containing 20 percent by weight of ethyl cellulose as an outer or wall material and 80 percent by weight of potassium chloride as a core material (Formula 80-20). The microcapsules had a mean particle size of 509μ.

In Vitro Dissolution Test Procedure Used

The dissolution test apparatus used in the examples consists of a 40-mesh stainless-steel basket placed on the end of a stirring shaft of a variable speed motor. The basket containing the capsule is immersed in 900 ml of water maintained at 37° C. and rotated at a speed of 100 rpm. The volume of the fluid is maintained constant by adding a volume equal to that removed for sampling purpose.

In Vivo Test Procedure for Comparing Effectiveness in Ligated-Partially Constricted Duodenum Large anesthetized cats are ligated at the pylorus and loosely ligated approximately 7 cm distal to the pylorus. A small stab wound is made about 1-2 cm distal to the loose ligature and a gelatin capsule containing the microencapsulated potassium salt or gelatin capsule containing a mixture of potassium chloride encapsulated with ethyl cellulose and hydrophilic surfactant is inserted and pushed upward past the loose ligature and positioned 2 to 6 cm above it. A glass rod 5 mm in diameter and longer than the depth of insertion is inserted through the stab wound upward to a point just past the loose ligature and the ligature is tightened and tied around the glass rod after which the glass rod is withdrawn. The cats are then placed at a 30-degree angle with the head at the highest level. After 4 hours exposure to the treatment the cats are sacrificed with Euthanasia Agent T-61, the duodenum removed, cut open washed with water and assessed for tissue damage such as inflammation, ulceration, etc. Observation is also made prior to washing on the amount of microcapsules remaining.

When the compositions of this invention; e.g., Example 5, were tested in the duodenum of cats in the foregoing manner, the microcapsules were moved out of the ligated area and no damage to tissue was found. In comparision, when a similar composition having no hydrophilic surfactant is tested, the microcapsules remain in the ligated area and tissue damage can be expected. Wax-coated tablets of potassium chloride tested in the same manner cause extensive tissure damage in the confined area.

The following examples are used to illustrate the present invention and are not intended to limit the invention in any way.

EXAMPLE 1

Seven hundred and fifty mg of microcapsules (above Formular 80-20) were filled by hand into #0 two-piece gelatin capsules provide a dosage form of 600 mg of potassium chloride in each capsule. The capsules were placed in the dissolution apparatus under the conditions indicated above. After one hour the microcapsules were observed and found to be substantially agglomerated. An assay of the dissolution fluid revealed that 13.2% by weight of the potassium chloride was dissolved in this period.

EXAMPLE 2

The same capsule formulation is given in Example 1 was prepared with the addition of 2 mg/capsule of the lubricant, magnesium stearate, to the formulation. The gelatin capsules were again filled by hand. The microcapsules agglomerated during the dissolution test. An assay of the dissolution fluid revealed that after one hour 4.4% by weight of the potassium chloride was dissolved.

EXAMPLE 3

The same capsule formulation as given in Example 2 was used. The gelatin capsules were filled by machine. The microcapsules again agglomerated during the dissolution test. An assay of the dissolution fluid revealed that after one hour 8.2% by weight of the potassium chloride was dissolved.

EXAMPLE 4

The same capsule formulation as given in Example 2 was used except that 0.6 mg/capsule of sodium lauryl sulfate was added to capsule formulation. The gelatin capsules were filled by hand. The microcapsules were rapidly released from the capsule and become free-flowing during the dissolution test. An assay of the dissolution fluid after one hour revealed that 18.1% by weight of the potassium chloride was dissolved. After 8 hrs, about 90% of the potassium chloride will have dissolved from the microcapasules.

EXAMPLE 5

The same capsule formulation as given in Example 4 was used. Gelatin capsules were filled by machine. The microcapsules were rapidly released from the capsule and became free-flowing during the dissolution test. An assay of the dissolution fluid after one hour revealed that 28.5% by weight of the potassium chloride was dissolved. After 8 hrs, 90% of the potassium chloride had been dissolved from the microcapsules.

EXAMPLE 6

The same capsule formulation as given in Example 2 was used except 3 mg/capsule of a mixture of 70% by weight of dioctyl sodium sulfosuccinate and 30% by weight of colloidal silicon dioxide was added to the capsule formulation. Gelatin capsules were filled by hand. The microcapsules were rapidly released from the capsule and became free-flowing during the dissolution test. An assay of the dissolution fluid after one hour revealed that 20% by weight of the potassium chloride was dissolved.

EXAMPLE 7

The same capsule formulation as given in Example 2 was used except a mixture of 3.0 mg of Polysorbate 80 (polyoxyethylene sorbitan monooleate) and 1.9 mg of colloidal silicon dioxide was added to the capsule formulation. Gelatin capsules were filled by hand. The microcapsules were rapidly released from the capsule and become free-flowing during the dissolution test. An assay of the dissolution fluid after one hour revealed that 17.1% by weight of the potassium chloride was dissolved.

EXAMPLE 8

The same capsule formulation as given in Example 2 was used except a mixture of 3.0 mg of Polysorbate 20 (polyoxyethylene sorbitan monolaurate) and 1.9 mg of colloidal silicon dioxide was added to the capsule formulation. Gelatin capsules were filled by hand. The microcapsules were rapidly released from the capsule and became free-flowing during the dissolution test. An assay of the dissolution fluid after one hour revealed that 16.9% by weight of the potassium chloride was dissolved.

It is understood that changes and variations may be made from the foregoing embodiments af the present invention without departing from the spirit and scope thereof as defined in the appended claims.

What is claimed is:

1. A pharmaceutical composition comprising a gelatin capsule containing therein a mixture comprising microencapsulated potassium salt and hydrophilic surfactant external to said microencapsulated salt.

2. A pharmaceutical composition comprising a gelatin capsule containing therein a mixture of microcapsules having an outer layer of polymeric material and core of potassium salt and hydrophilic surfactant external to said microcapsules.

3. The composition as defined in claim 2 where in the surfactant has a HLB number in excess of 10 and is present in an amount of from about 0.05 to 5.0 percent by weight.

4. The composition as defined in claim 3 wherein the polymeric material is ethyl cellulose and the potassium salt is potassium chloride.

5. A pharmaceutical composition for treating potassium deficiency in monogastric animals comprising a gelatin capsule containing therein a mixture comprising controlled-released microencapsulated potassium salt and hydrophilic surfactant external to said microencapsulated salt, said microencapsulated salt containing 3 to 50 weight percent polymeric material and said hydrophilic surfactant being present in an amount within the range of 0.05 to 5.0 weight percent based on the weight of said microencapsulated salt sufficient to increase flowability of said microencapsulated salt in a partially obstructed alimentary tract of a monogastric animal.

6. A pharmaceutical composition of claim 5 wherein the surfactant is in an amount of 0.05 to 1.0 weight percent based on the weight of the microencapsulated salt.

7. A method for the treatment of potassium deficiency or prevention of potassium depletion in a human which comprises administering to said human an effective amount of potassium, said potassium being administered in the form of a non-toxic pharmaceutical comprising a gelatin capsule containing a mixture comprising microencapsulated potassium salt and hydrophilic surfactant external to said microencapsulated salt.

8. A method for the treatment of potassium depletion or prevention of potassium depletion in a human which comprises administering to said human an effective amount of potassium, said potassium being administered in the form of a non-toxic pharmaceutical composition comprising a gelatin capsule containing a mixture comprising microcapsules having an outer layer of ethyl cellulose and a core of potassium chloride and a hydrophilic surfactant external to said microcapsules.

9. The method as defined in claim 6 wherein the surfactant has a HLB number in excess of 10 and is present in the composition in an amount of from about 0.05 to 5.0 percent by weight.

10. The method as defined in claim 7 wherein the polymeric material is ethyl cellulose and the potassium salt is potassium chloride.

* * * * *

UNITED STATES PATENT AND TRADEMARK OFFICE
CERTIFICATE OF CORRECTION

PATENT NO. : 4,259,315

DATED : March 31, 1981

INVENTOR(S) : Irwin Lippmann; Shankar D. Popli, Larry G. Miller; Louis G. Bell

It is certified that error appears in the above-identified patent and that said Letters Patent is hereby corrected as shown below:

Column 8, lines 11 and 12:
In claim 2, line 5, change "externaul" to read "external."

Signed and Sealed this

Twenty-first Day of January, 1992

Attest:

HARRY F. MANBECK, JR.

Attesting Officer

Commissioner of Patents and Trademarks